United States Patent [19]

Beineke

[11] Plant 4,971

[45] Jan. 4, 1983

[54] BLACK WALNUT TREE

[75] Inventor: Walter F. Beineke, West Lafayette, Ind.

[73] Assignee: Purdue Research Foundation, West Lafayette, Ind.

[21] Appl. No.: 254,908

[22] Filed: Apr. 16, 1981

[51] Int. Cl.[3] ..... A01H 5/03

[52] U.S. Cl. ..... Plt./32

[58] Field of Search ..... Plt./32

*Primary Examiner*—Robert E. Bagwill

*Attorney, Agent, or Firm*—John R. Nesbitt

[57] ABSTRACT

A new and distinct cultivar of black walnut tree (*Juglans nigra L.*) which is distinctly characterized by rapid growth rate, strong central stem tendency, average time of leafing, and excellent straightness (little sweep and few crooks) thereby producing excellent timber qualities. The new variety has good nut qualities as well as abundant annual to biennial crops of large-sized nuts, begins nut-bearing early in life of tree, average 2 nuts per cluster, and produces kernels which exceed about twenty (20) percent of nut weight. The nuts are large and ripen in mid-season. The pistillate flowers mature early while pollen maturity is late. In most years there is no overlap in female and male flowering. Flowering begins very early in the life of the tree. This new variety of black walnut tree was discovered by the applicant near Silverville in Lawrence County, Ind., in a cultivated area. It occurred as a wild tree growing on land managed for timber-growing purposes and was discovered in the course of a search for unique and high quality black walnut trees to be utilized in breeding for outstanding timber producing potential. This selection has been designated as BW49 in records maintained on the performance of grafts made from the original selection and will be known henceforth as Lawrence-1.

3 Drawing Figures

BACKGROUND OF THE INVENTION

Figure 1:
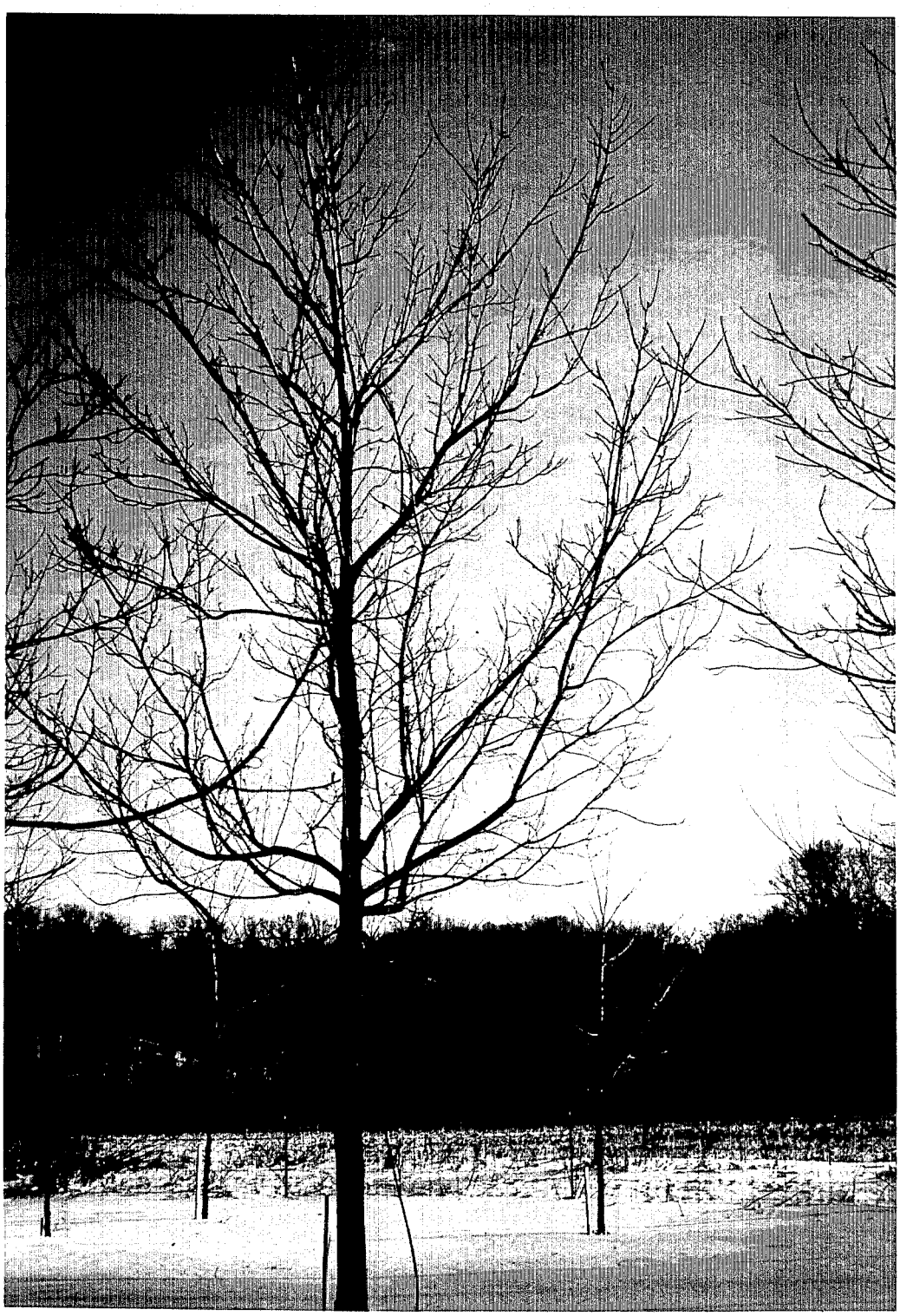
FIG. 1 is a photograph showing the timber form of Lawrence-1.
Figure 2:
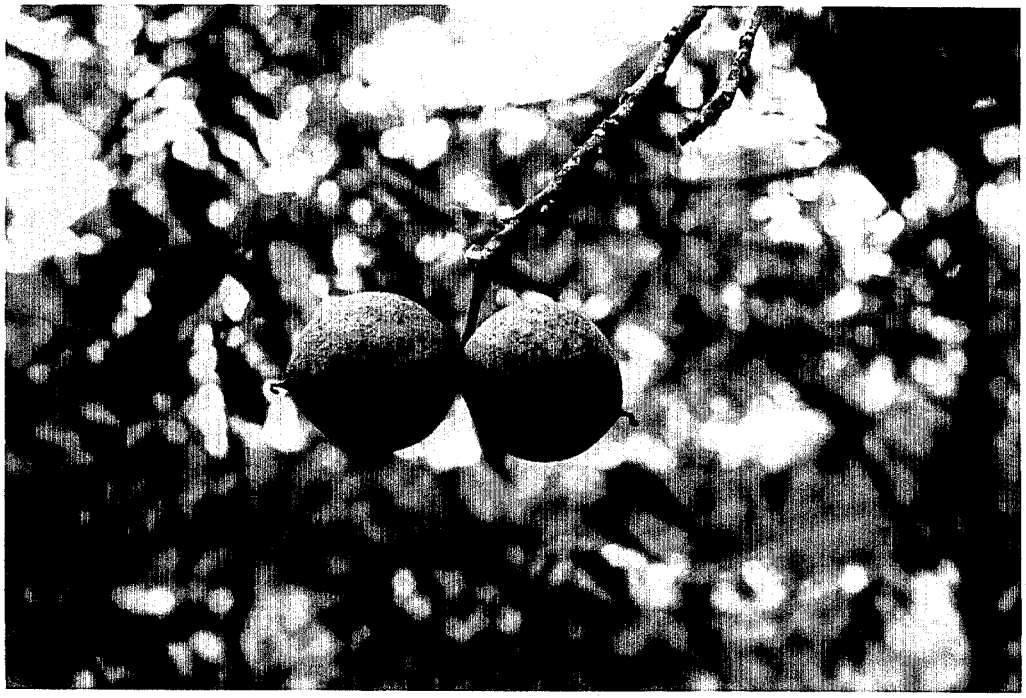
FIG. 2 is a photograph showing a twig with nuts attached from Lawrence-1.
Figure 3:
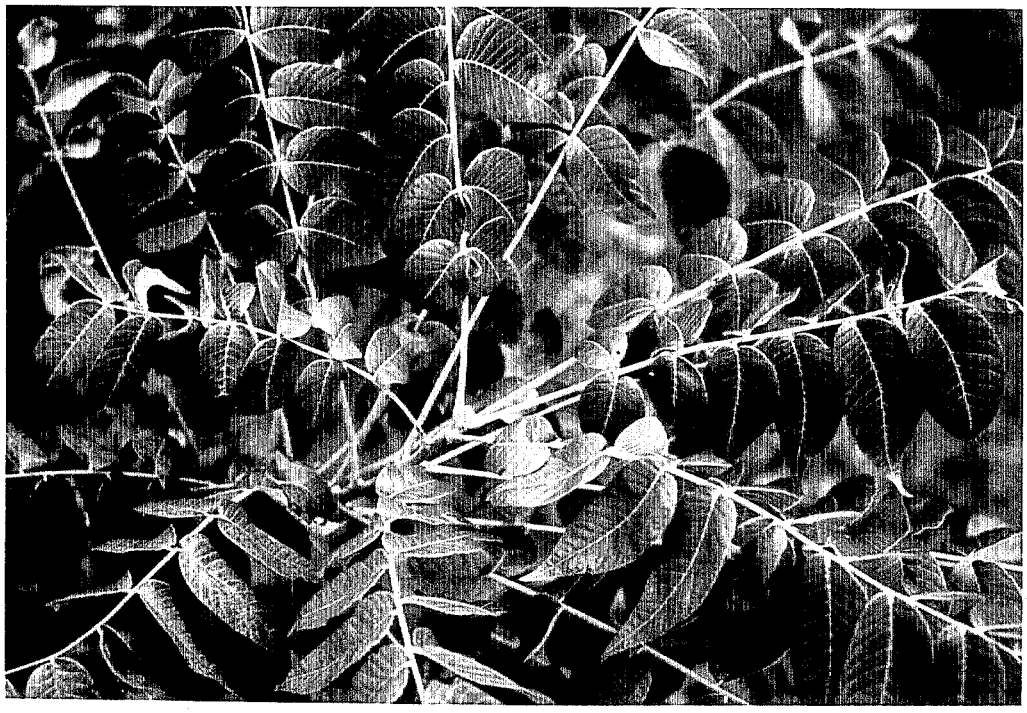
FIG. 3 is a photograph showing leaves of Lawrence-1.

After the original clone was selected, and assigned an identity number of BW49, the aforesaid tree was reproduced by collecting scions from it and grafting these onto common black walnut rootstocks at Martell Forest, Purdue University. These asexual reproductions ran true to the parent tree and to each other in all respects.

The botanical details of this new and distinct variety of walnut tree are as follows:

Tree:

*Size.*—Large.

*Vigor.*—Vigorous.

*Growth rate.*—Rapid growth, but slower than Purdue 1, 2, and 3–5% larger in diameter than the average of selected clones planted the same year, 8% taller than the average, and 16% more cubic foot volume than the average.

*Form.*—Excellent timber form nearly as good as Purdue 1 — 34% straighter than average on a rating scale of 1 to 5. Few crooks. Strong central stem tendency.

Trunk:

*Bark.*—Dark brown to gray.

*Texture.*—Interlacing ridges.

Branches:

*Diameter.*—Average — large.

*Length.*—Long.

*Branch angle.*—Lower branches — average — 60 deg.

*Foliage.*—Quantity — Abundant. Density — Heavy.

Leaves:

*Compound leaves.*—Size — longer than average; average length — 18".

*Leaflets.*—Size — large; average length — 4¼"; average width — 1½"; average number of leaflets — 17; shape — lanceolate; acutely pointed. Thickness — thin; Texture — smooth; Margin — serrated; Petiole — short; Color — Topside — dark green; Underside — light green.

*Anthracnose resistance.*—Excellent, much better than average on a rating scale of 1 to 5.

*Time of leafing.*—About average.

Flowering habit:

*Age at which tree starts producing catkins.*—Very early.

*Number of catkins produced.*—Abundant.

*Size of catkins.*—Average.

*Time of pollen shed.*—Late.

*Age at which time tree starts producing pistillate flowers.*—Very early.

*Number of pistillate flowers produced by young trees.*—Abundant.

*Number of pistillate flowers produced by mature trees.*—Abundant.

*Lateral shoots producing pistillate flowers.*—Abundant some years.

*Number of pistillate flowers per inflorescence.*—2–3.

*Timing of pistillate flower receptivity.*—Early.

*Coincidence of staminate and pistillate bloom.*—Seldom.

Nut crop:

*Bearing.*—Annual to biennial.

*Productivity.*—Heavy.

*Ripening period.*—Mid-season.

*Evenness of maturity (period between first and last nuts are ready for harvest).*—Even.

*Quality.*—Very good.

*Distribution of nuts on tree.*—Throughout.

Hull:

*Outer surface.*—Smooth — a few warts.

*Form.*—Nearly rounded both ends.

*Thickness.*—Thick.

*Size.*—Large; average length — 2 5/16"; average diameter in suture plane — 2"; average diameter cheek to cheek — 2 7/32".

Nut:

*Size.*—Medium; average length — $1\frac{3}{8}$"; average diameter in suture plane — $1\frac{1}{8}$"; average diameter cheek to cheek — $1\frac{1}{2}$".

*Uniformity of size.*—Some variability.

*Form.*—Round — flattened in suture plane.

*Blossom end.*—Rounded.

*Basal end.*—Rounded.

*Weight.*—Dry weight of ten nuts — 159.6 gm; dry weight of ten kernels — 32.2 gm; average percentage kernels to nut — 20.2%.

*Thickness of shell.*—Thin.

*Fill.*—Good.

Kernel:

*Size.*—Large.

*Plumpness.*—Plump.

*Shrivel.*—None.

*Flavor.*—Good.

*Color.*—Light.

The walnut tree and its nuts herein described may vary in slight detail due to climatic and soil conditions under which the variety may be grown; the present description being of the variety as grown near West Lafayette, Ind.

I claim:

1. A new and distinct variety of black walnut tree substantially as illustrated and described, which has excellent timber quality, is fast growing, has strong central stem tendency, little sweep, few crooks; average in time of leafing, pistillate flowers early, pollen sheds mid-season, produces abundant annual crops of large-sized nuts; averages 2 per cluster, the percentage of weight of kernel to nut averages approximately twenty (20) percent; nut bearing begins early in life of tree.

* * * * *